US00PP07960P

United States Patent [19]

Hanes

[11] Patent Number: Plant 7,960

[45] Date of Patent: Sep. 1, 1992

[54] GERANIUM NAMED AMERICANA WHITE

[75] Inventor: Mitchell Hanes, Morgan Hill, Calif.

[73] Assignee: Goldsmith Seeds, Inc., Gilroy, Calif.

[21] Appl. No.: 678,549

[22] Filed: Mar. 29, 1991

[51] Int. Cl.[5] ..... A01H 5/00

[52] U.S. Cl. ..... Plt./87.12

[58] Field of Search ..... Plt./68, 87.12

[56] References Cited

U.S. PATENT DOCUMENTS

P.P. 7,392 12/1990 Schumann ..... Plt. 68

*Primary Examiner*—Howard J. Locker

[57] ABSTRACT

A new Geranium cultivar particularly distinguished by its deep green foliage, its clean white semi-double flowers, and its vigorous growth habit; the plant reaching a height of 15–20 cm. as a potted plant.

1 Drawing Sheet

BACKGROUND OF THE NEW PLANT

The present invention comprises a new and distinct cultivar of Geranium, botanically known as *Pelargonium hortorum* Bailey, and hereinafter referred to by the cultivar name Americana White. The new cultivar is a hybrid seedling resulting from a controlled crossing of a single flowered salmon colored seed parent and a semi-double flowered salmon colored pollen parent, at the company nursery in Gilroy, Calif., both parents having been known to carry the genes necessary for white flower color.

This new Geranium plant is a product of a planned breeding program intended to create new Geranium cultivars with white colored flowers, semi-double flower form, green foliage, vigorous growth and superior cutting productivity.

The new cultivar was developed in 1988 and has been repeatedly reproduced by cuttings in Gilroy, Calif. and in Guatemala over a two year period. It has also been trialed at Okemos, Mich. and in all cases this plant has been found to retain its distinctive characteristics through successive propagations; and this novelty appears to be firmly fixed.

DESCRIPTION OF THE DRAWING

This new Geranium plant is illustrated by the accompanying photographic drawing which shows blooms, buds, and foliage of the plant in full color, the colors shown being as true as can be reasonably obtained by conventional photographic procedures.

DESCRIPTION OF THE NEW CULTIVAR

The following detailed descriptions set forth the distinctive characteristics of Americana White. The data which defines these characteristics were collected from asexual reproductions carried out in Gilroy, Calif. The plant history was taken on 20 week old plants, blossomed under natural light in a greenhouse and color readings were taken in the greenhouse (in Gilroy, CA) on May 29, 1990 at 2 P.M. under ambient light. Color references are primarily to The R.H.S. Colour Chart of The Royal Horticultural Society of London, England.

THE PLANT

Classification:

*Botanical.*—*Pelargonium hortorum* Bailey.

*Commercial.*—Zonal Geranium.

Form: Open, upright.

Height: 15 to 20 cm., as a 5½ inch potted plant, excluding blooms.

Growth: Fast-rooting and vigorous with early flowering.

Strength: Plant is strong with a deep green foliage that holds up well under stress conditions when other white flower varieties get pale foliage. Good shipping ability as rooted or unrooted cuttings.

Foliage: Abundant quantity.

Leaves:

*Size.*—Diameter about 8–10 cm.

*Shape.*—Rounded cordate with occasional upfolding between veins.

*Margin.*—Irregularly crenate.

*Texture.*—Leathery and pubescent on both surfaces, especially along veins.

*Ribs and veins.*—Distinctly palmate, 3.5 to 5.5 cm. long.

*Color.*—Upper side: Deep green with a darker green zone. Underside: Lighter green color. Ribs and veins not prominently different from upper surface.

*Petioles.*—Range from about 4 to 8 cm. in length.

THE BUD

Size:

*Diameter.*—About 7 mm.

*Length.*—About 1.8–2.0 cm. at time of bud opening.

Shape: Pointed ovoid.

Color: When sepals first divide, R.H.S. 155-B.

Sepals: Five (sometimes six) in number, flat behind petals. Pointed linear lanceolate, R.H.S. 143-C in an open flower.

THE FLOWER

Blooming habit: Continuous throughout the year.

Size: Approximately 4.5 cm. diameter, 0.5 cm. deep, irregularly radially symmetrical.

Form: Cup-shaped when bloom first opens, later flattening to shallow cup-shape with maturity.

Petals: Five imbricate outer petals, 1.9–2.1 cm. wide and approximately 2.1 cm. long. Three to five inner smaller petaloids of varying shape. Both the outer petaloids and inner petaloids are white R.H.S. 155-D. Veins same as interveinal regions. Color changing little with age. Underside of petals same color as the upper side. Petals and petaloids soft and satiny.

Pedicel: Approximately 2.7–3.5 cm. in length.

Persistence: Nonshattering flower.

INFLORESCENSE

Type: An umbel composed of approximately 30 flowers, erect or laterally ascending.

Peduncle: Approximately 4–7 cm. in length, mostly 6 cm. and green in color.

REPRODUCTIVE ORGANS

Stamens:

*Anthers.*—Six to nine positioned below the mature stigma, dull red prior to anthesis.

*Filaments.*—White through the full length.

*Pollen.*—Orange in color.

Pistil:

*Number.*—One.

*Length.*—Approximately 9 mm.

*Style.*—Length: About 3 mm., color: white.

*Stigma.*—Five or six linear lobes of near equal length, curling back toward ovary, white in color.

*Ovaries.*—At anthesis, densely pubescent with white hairs, oblong in shape and green drying to a light brown at maturity.

Fruit: Partially fertile.

I claim:

1. A new and distinct cultivar of Geranium plant substantially as herein shown and described, named Americana White, that is characterized by deep green foliage with a band of darker green zonation, white flower color, and semi-double flowers on large umbels, the plant being fast-rooting and having a vigorous growth habit.

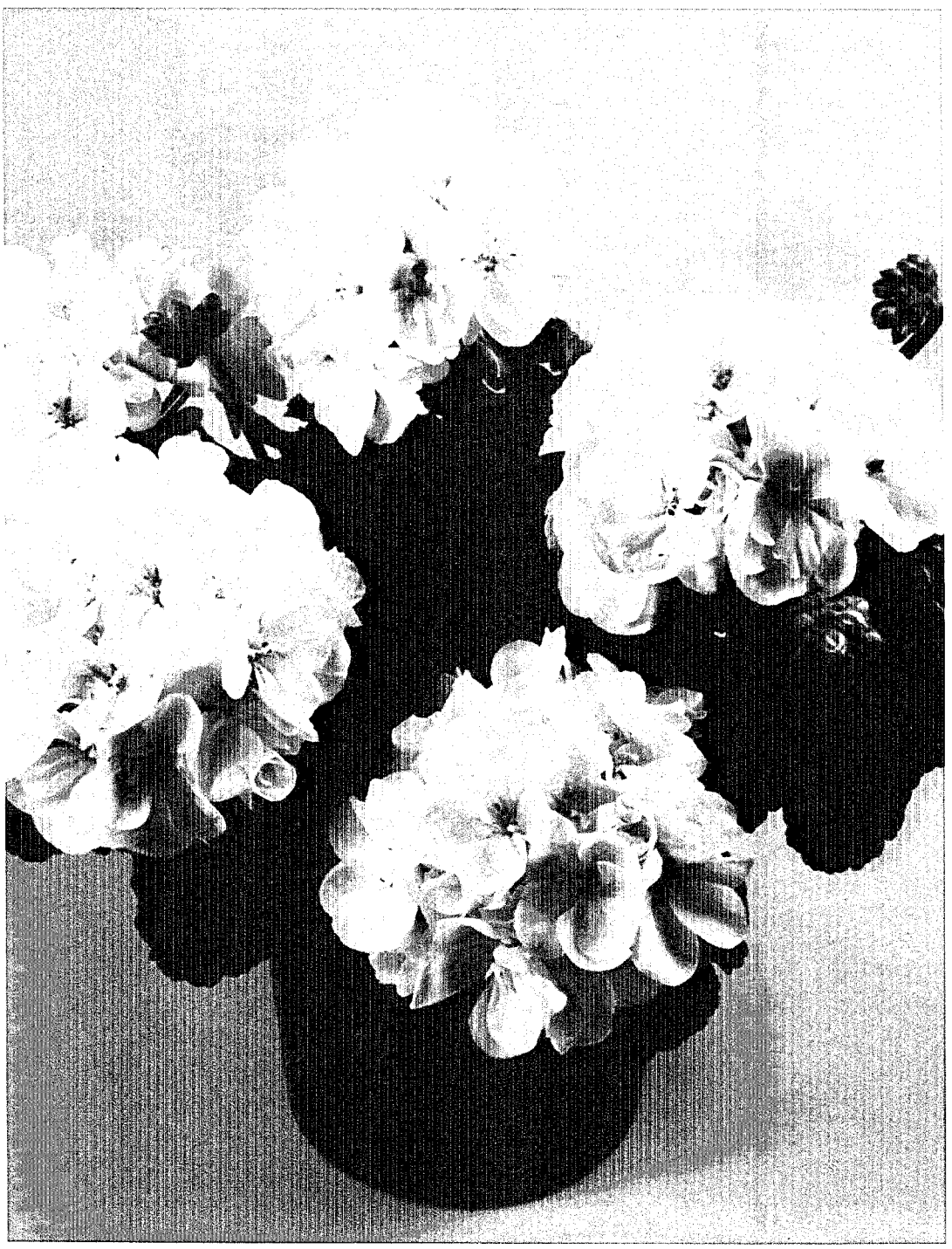

* * * * *